United States Patent [19]

Dulebohn et al.

[11] Patent Number: 5,007,913
[45] Date of Patent: Apr. 16, 1991

[54] APPARATUS AND METHOD FOR IMPLANTATION OF INTRAOCULAR LENSES

[75] Inventors: David H. Dulebohn, Tonka Bay; Winston R. Lindberg, Plymouth, both of Minn.

[73] Assignee: Alcon Surgical, Inc., Fort Worth, Tex.

[21] Appl. No.: 409,329

[22] Filed: Sep. 19, 1989

[51] Int. Cl.$^5$ .................................................. A61F 9/00
[52] U.S. Cl. .................................... 606/107; 623/6
[58] Field of Search ............... 606/107, 142, 207, 206, 606/205; 433/159; 294/99.2; 128/898; 623/6

[56] References Cited

U.S. PATENT DOCUMENTS

| | | | |
|---|---|---|---|
| 450,266 | 4/1891 | Traux | 294/99.2 |
| 1,837,277 | 12/1931 | Lund . | |
| 4,198,980 | 4/1980 | Clark | 606/107 |
| 4,303,268 | 12/1981 | Davidson | 294/99.2 |
| 4,325,375 | 4/1982 | Nevyas | 606/207 |
| 4,462,404 | 7/1984 | Schwarz et al. | 606/142 |
| 4,573,998 | 3/1986 | Mazzocco | 623/6 |
| 4,681,102 | 7/1987 | Bartell | 606/107 |
| 4,702,244 | 10/1987 | Mazzocco | 623/6 |
| 4,759,359 | 7/1988 | Willis et al. | 606/107 |
| 4,769,034 | 9/1988 | Polcy | 623/6 |
| 4,785,810 | 11/1988 | Baccala et al. | 606/207 |
| 4,791,924 | 12/1988 | Kelman | 128/303 R |
| 4,813,956 | 3/1989 | Gupta | 623/6 |
| 4,813,957 | 3/1989 | McDonald | 623/6 |
| 4,836,201 | 6/1989 | Patton et al. | 623/6 |
| 4,844,065 | 7/1989 | Faulkner | 606/107 |

FOREIGN PATENT DOCUMENTS

| | | |
|---|---|---|
| 255952 | 7/1985 | France . |
| WO82/01646 | 5/1982 | PCT Int'l Appl. . |
| 2191439A | 12/1987 | United Kingdom . |

OTHER PUBLICATIONS

"Intracameral lenses Made of Hydrocolloid Acrylates", by Dreifus, Wichterle and Lim, of II. Eye Clinic, Charles University from Sc. Oftamologie 16 (2), 454–459 (1960) (translation from Czech).
"Folding and Inserting Silicon Intraocular Lens Implants", by Gerald D. Faulkner, M.D. *J. Cataract Refract Surf*, vol. 13, Nov. 1987, pp. 678–681.
"Pathologic Findings of an Explanted Silicone Intraocular Lens", by Newman, McIntyre, Apple, Deacon, Popham, and Isenbert; *J Cataract Refract Surg*, vol. 12, May 1986, pp. 292–297.

*Primary Examiner*—C. Fred Rosenbaum
*Assistant Examiner*—William W. Lewis
*Attorney, Agent, or Firm*—Zarley, McKee, Thomte, Voorhees & Sease

[57] ABSTRACT

An apparatus and method for implantation of intraocular lenses includes a resilient tubular sling which is positionable over parallel working ends of a crossover forceps. The sling allows an intraocular lens to be folded or curled up therein and held in that folded up position with the forceps tips in a closed position. The forceps presents a narror-in-cross-section moving crossover point behind the tips to allow the forceps tips to be inserted through a small incision in the eye, and then open to release the lens once within the eye. By maintaining the crossover point at the small incision, the forceps can release the lens even though it requires the opening of the forceps tips to a position wider than the incision in the eye. The resilient sling holds the folded lens compactly during movement through the small incision, and assists in urging a controlled release of the lens into the eye. The sling also avoids having to handle the lens with the forceps tips prevents damage to the lens.

36 Claims, 6 Drawing Sheets

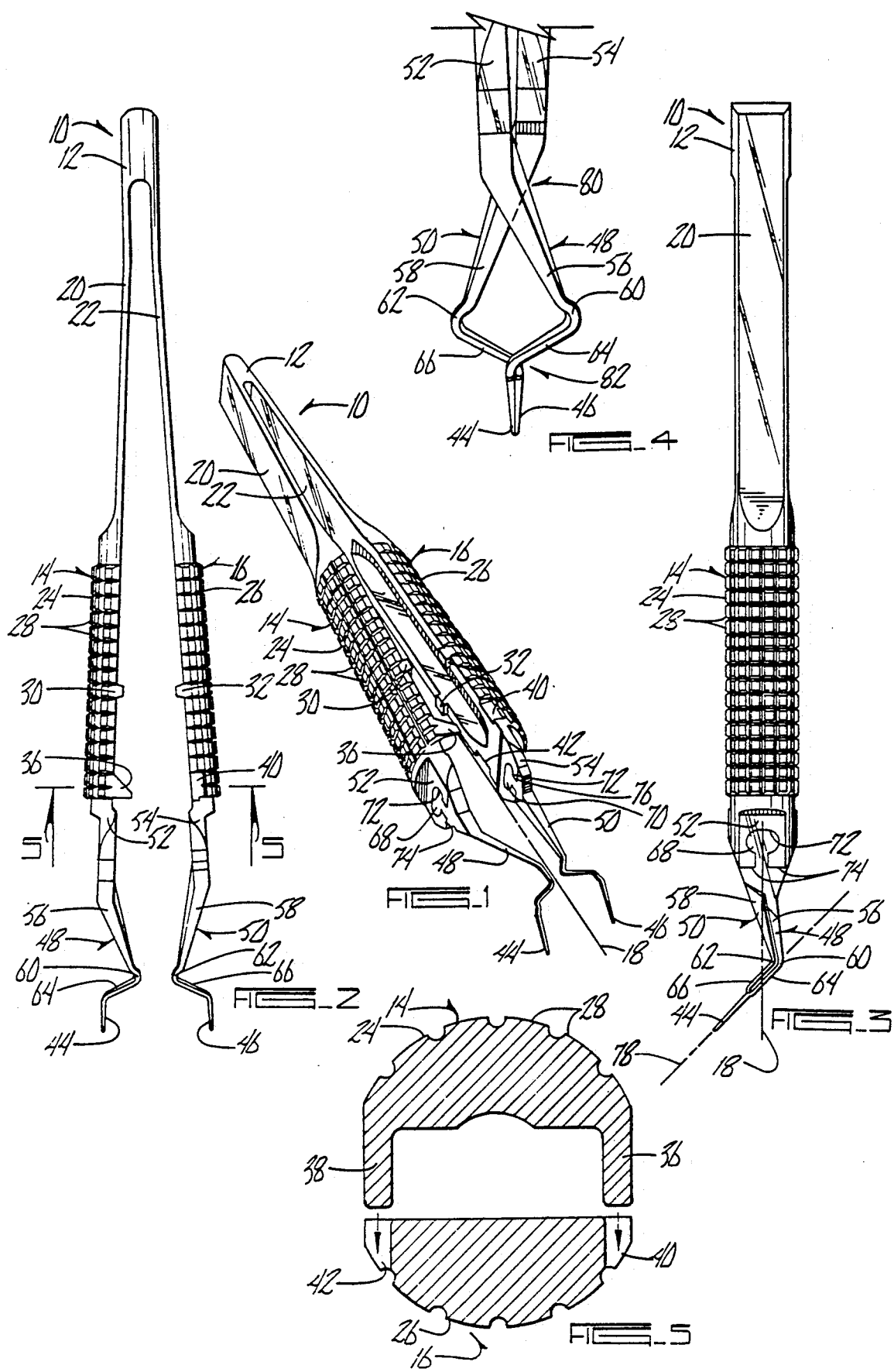

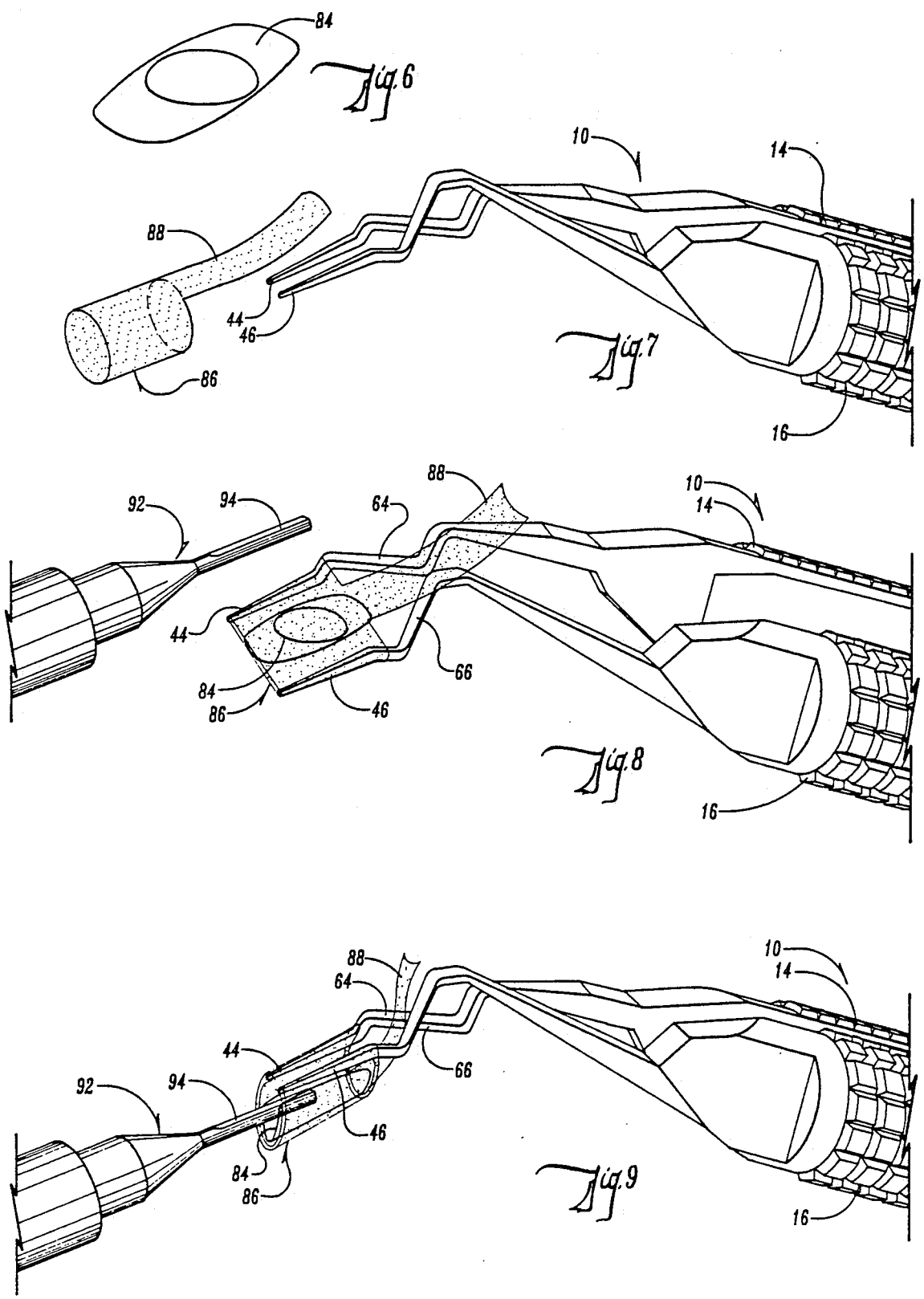

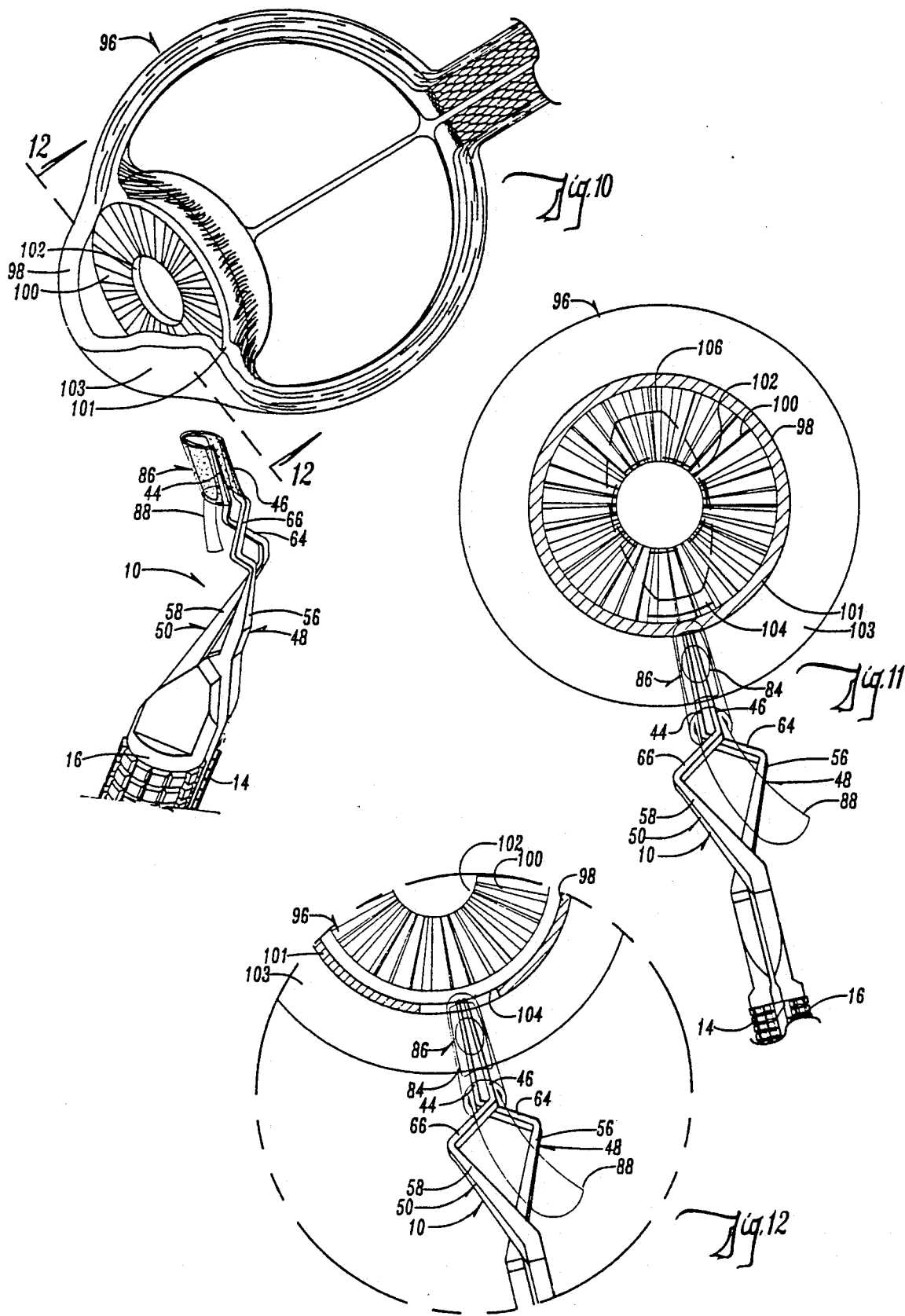

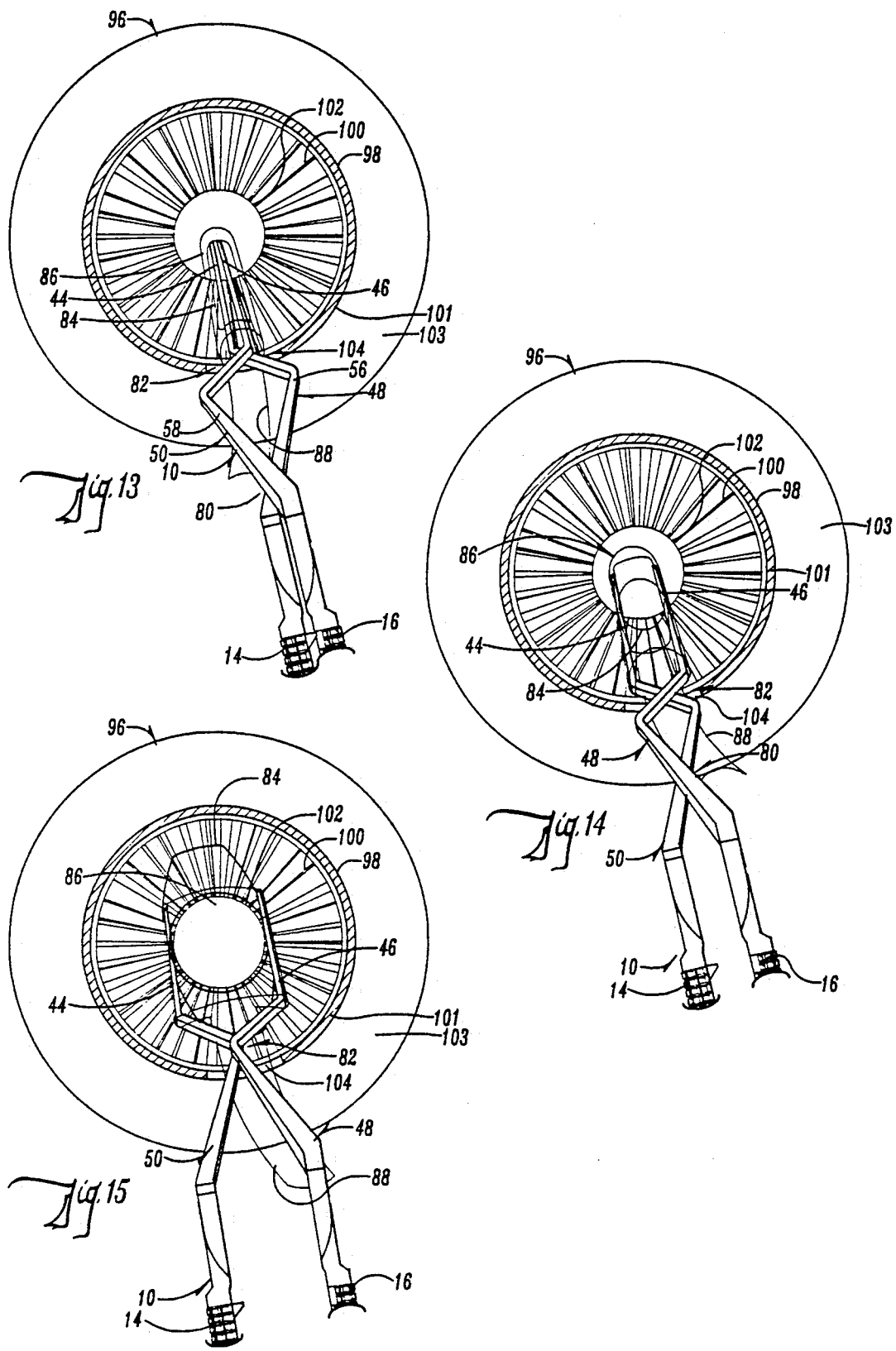

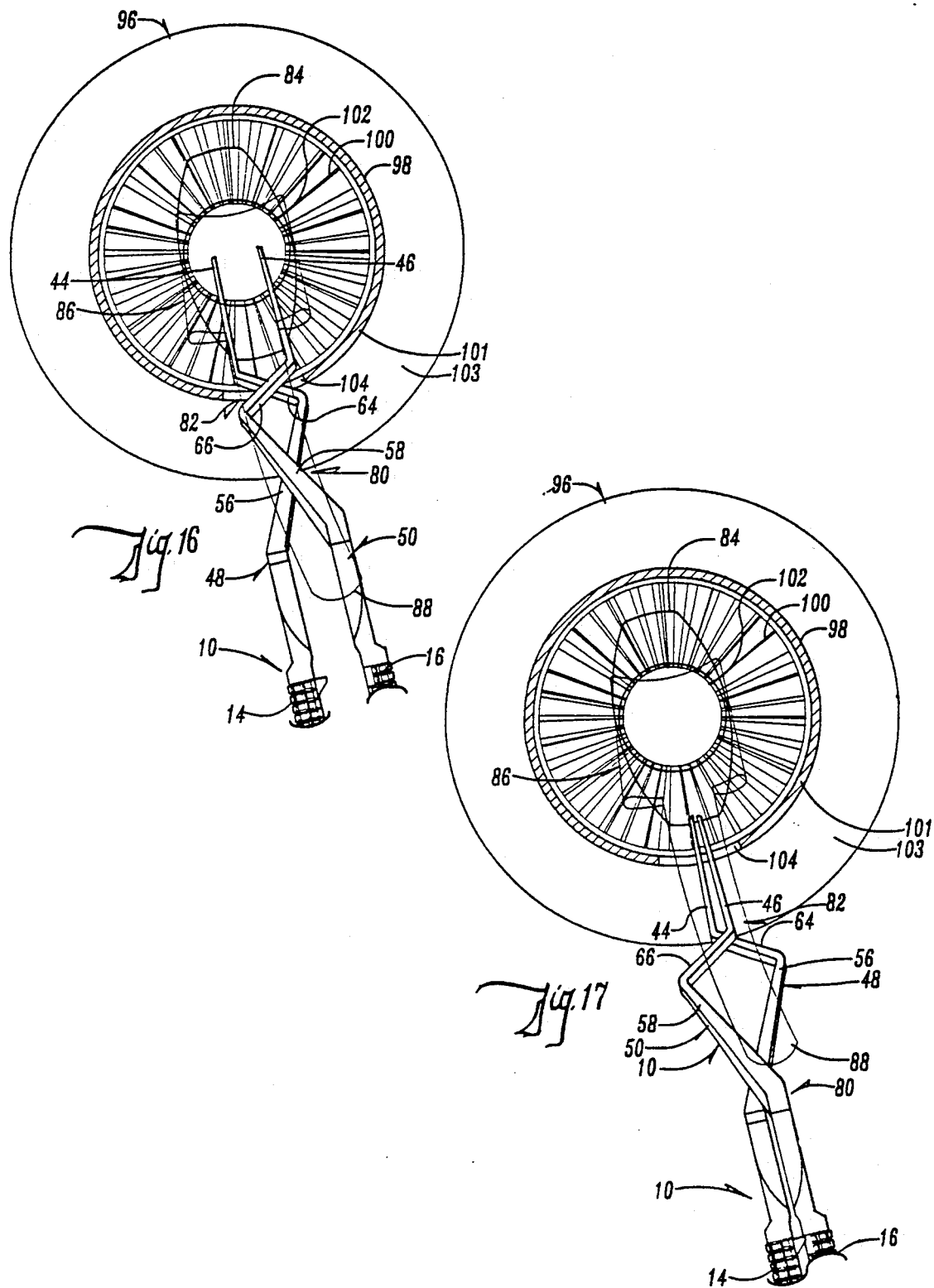

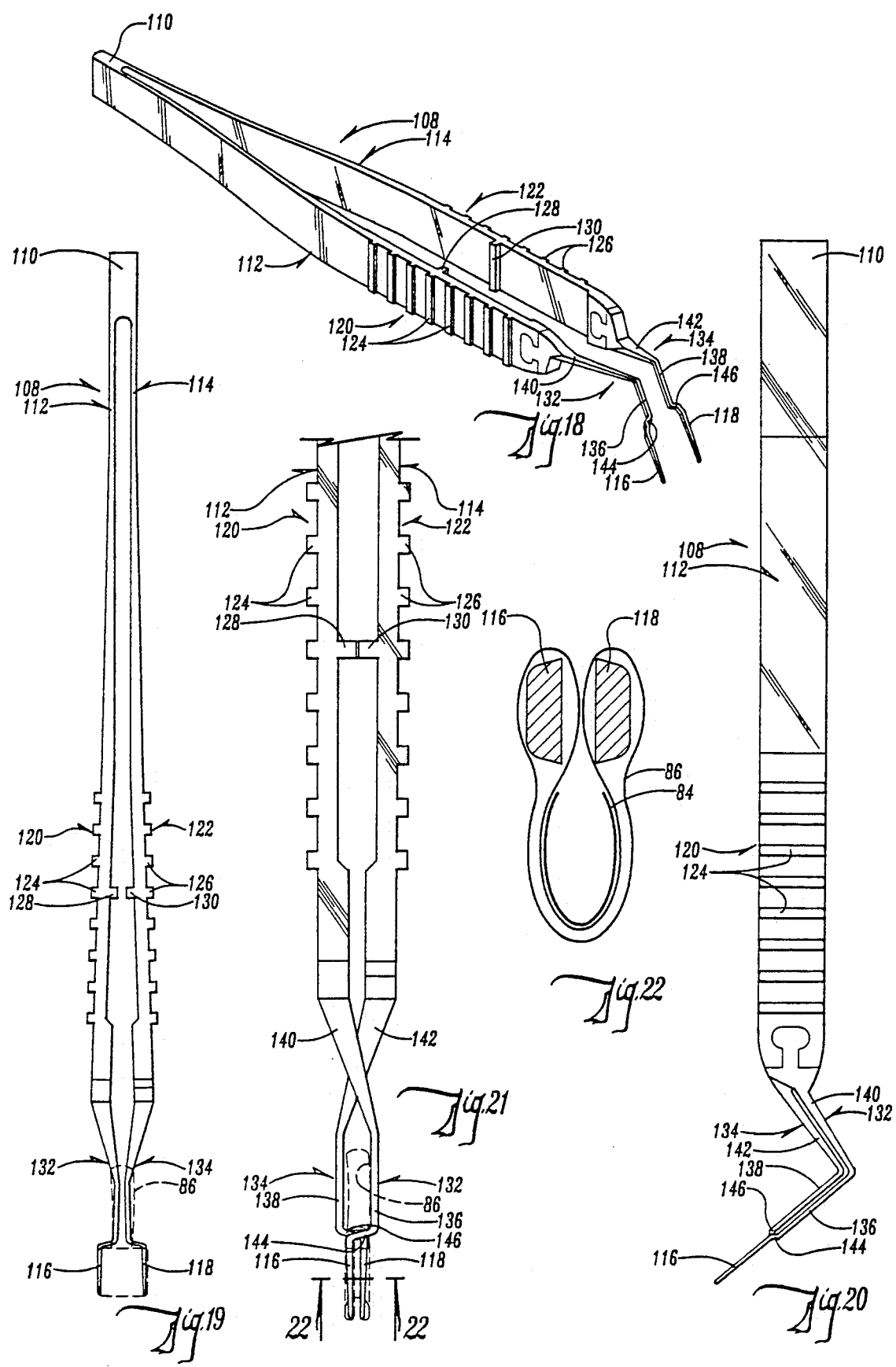

APPARATUS AND METHOD FOR IMPLANTATION OF INTRAOCULAR LENSES

BACKGROUND OF THE INVENTION

A. Field of the Invention

The present invention relates to an apparatus and method for implanting intraocular lenses in ophthalmic surgical procedures. More particularly, this invention relates to a means and method for implanting intraocular lenses made from a relatively soft, pliable foldable material through a very small surgical incision.

B. Problems in the Art

Working within the human eye requires that any incision be kept to minimum size. This conflicts with the need to use surgical instruments and tools in performing surgery within the eye, including implanting intraocular lenses.

Microsurgical tools are utilized in eye surgery. As the term "microsurgical" implies, because of the small frame work and intricate nature of surgery on the eye, the microsurgical tools or instruments must at once both have control portions (usually handles) which are easily grippable and maneuverable by the surgeon's hands and fingers, and have working end tips which are down-sized or basically miniaturized. The size and shape of instrument tips can be made so as to give the surgeon grasping, positioning, and retrieval capabilities on a very small scale. Conventional microsurgical forceps, having parallel spaced apart handle and tip combinations, work adequately for many requirements of ophthalmic surgery.

However, in ophthalmic surgery, even conventional microsurgical forceps are many times deficient. Where intrusion is needed to gain access into the interior of the eye, such as with delivering an artificial intraocular lens for implantation, conventional forceps basically require that the surgical incision or wound must be at least as wide as the open width of the forceps tips. This is required to insert and release an object into the eye and retrieve objects from the eye, which necessitates opening and closing of the tips within the eye. In other words, microsurgical forceps, when closed, generally present a fairly narrow and small cross section. They could easily be inserted through a small incision. However, in order to open the forceps tips to perform any grasping or releasing function within the eye, or to allow insertion of an object gripped in the forcep's tips, the incision must be wide enough to accommodate the open position of the tips.

In ophthalmic surgery, smaller wounds or incisions cause less trauma, reduced problems and scarring, and promote faster healing. Many forceps can be inserted through a very narrow wound, but can not be opened up inside the cavity because movement is restricted by the small size of the incision. Further, a narrow incision does not allow insertion of an object wider than the wound.

With conventional microsurgical forceps, therefore, the incision has to be made large enough to provide the needed opening and closing movement of the forceps, and also to accommodate the passage of objects that must be inserted into the cavity.

A specific example in ophthalmic surgery is where an artificial replacement lens (referred to in the art as an "intraocular lens") is to be delivered into the interior cavity of the eye. Such a lens, of course, has a certain length, width and thickness. Generally these lenses are thin in thickness, yet by comparison substantial in length and width; being somewhat rectangular or elliptical in shape. Even grasping the lens on its edges across its width requires a wound approximately as wide as the lens to insert the lens into the eye. In fact, the wound many times must be slightly larger to enable the forceps tips to pass and to allow the forceps tips to release the lens in the eye.

Recent developments in soft intraocular lenses allow that the lens can be folded or rolled into a small, somewhat cylindrical form. With the advent of the use of intraocular lenses made from relatively soft, flexible materials, such as silicone or hydroxyethylmethacrylate, has furthermore come the suggestion that these lenses could be folded or otherwise manipulated to facilitate implantation of the lenses in the eye. Reference is made to the following publications for further background information in this regard: Dreifus, Wichterle, and Lim, of II. Eye Clinic, Charles University, Prague, Czechoslovakia, "INTRACAMERAL LENSES MADE OF HYDROCOLLOID ACRYLATES", from Cs. oftamologie, 16(2), 454–459 (1960); U.S. Pat. No. 4,664,666 (Barrett); U.S. Pat. No. 4,573,998 (Mazzocco); and U.S. Pat. No. 4,813,957 (McDonald). In this form, the lens can be inserted into the eye through a much smaller incision than would otherwise be required.

The problem then becomes how to fold the lens and retain it undamaged for delivery into the eye, and then release it when inside the eye. The lens must be released slowly, and restrained during release so that it does not pop out of the restraining device.

It would therefore be advantageous to have an apparatus which could pass through a smaller opening and still be able to open and release while inserted through the opening, which would be allowed to be smaller than the width of the forceps tips when in a substantially open position.

It would furthermore be advantageous to develop a method to insert an artificial lens into the eye through as small an opening as possible.

Although the advent of soft intraocular lenses has made it possible to consider folding the lenses to facilitate the use of a smaller surgical incision, there are still significant problems associated with the folding or other manipulation of soft lenses and the implantation of such lenses in the folded or manipulated state. For example, the same properties which allow the lenses to be folded also make the lenses susceptible to being damaged due to contact with folding instruments such as forceps. The damage can be in the form of scratches, tears or other physical damage to the lenses, as well as deterioration of the optical properties of the lenses. In addition, it should be borne in mind that the implantation of intraocular lenses is a very delicate procedure which is performed with the aid of a microscope. The lenses are quite small (i.e., typical diameter of optical portion about 6 millimeters and overall length/width of 12 millimeters), and are therefore difficult to handle under the best of circumstances. The handling of the lenses with conventional surgical instruments, such as forceps, can be much more difficult if attempts are made to fold or otherwise manipulate the lenses.

Present ophthalmic surgical procedures present problems with respect to insertion of soft intraocular lenses through as small of incision as possible along with providing a controlled release and unfolding of a lens once inside the eye. The surgeon must be able to easily and reliably control operation and orientation of the instrument or instruments used in such procedures; but at the same time introduce both the tool or apparatus and the artificial lens through a very small incision; and controll-ably release the lens into the eye.

Accordingly, there is a need for an improved apparatus and method for folding a soft intraocular lenses and releasing the lens for implantation in the eye using a small incision and with minimized risk of damaging the lens or the eye. The present invention is directed to fulfillment of this need.

These and other objects, features, and advantages of the present invention will become more apparent with reference to the accompanying specification and claims.

SUMMARY OF THE INVENTION

An apparatus and method for implantation of intraocular lenses is presented. The method includes steps to allow a soft, pliable intraocular replacement lens to be folded into a configuration which can be inserted into the eye through a small incision or wound. The folding of the lens and the transporting of the lens from outside of the eye to the interior of the eye is accomplished without grasping the lens directly and solely with instrument tips, thereby avoiding the risk of damaging the lens. A resilient sling or carrier is mounted to a microsurgical tool; preferably a specialized forceps. The lens is folded upon itself, basically in half within the sling, which retains the folded lens without direct contact or direct gripping force of the forceps tips. The folded lens assumes a small cross-sectional width, compared to its unfolded state. It is contained in a shape folded upon itself; preferably a somewhat cylindrical shape. It is also held tightly within the folded state by the resilient nature of the sling or carrier.

By preparing the lens in this way, it can be inserted through a small incision in the eye. The incision is small in length as compared to what its length would need to be in the case of inserting an unfolded lens. The method of the invention then also presents steps to allow the lens to be inserted through the small wound, transported to the desired position within the eye, and then controllably released within the eye. Finally, the forceps and sling can be removed through the small incision to allow the intraocular lens implantation to proceed.

The method of using the invention is particularly adapted for inserting soft artificial lenses into an eye in cataract surgery. By utilizing the forceps and sling, the potential for damage to the lens is therefore greatly reduced. The sling further allows easier holding of the lens during insertion, as opposed to trying to grip it with forceps tips or other microsurgical instruments.

An embodiment of the invention uses an elastomeric tubular sleeve or sling mountable around and across the opened working end tips of a crossover forceps to produce what will be referred to herein as a foldable platform. The artificial lens, of certain flexibility and resiliency, is laid longitudinally along the platform. By use of a depressor tool or other means, the lens is pressed down within the platform of the sling as the forceps tips are brought together. The lens is thereby folded or curled up within the sleeve. The resilience of the sling and the closed tips of the forceps compacts and holds the lens in the sling and presents a much smaller width then if the lens was merely held across its width in a forceps tips.

The forceps tips with the folded lens can then be inserted through the small wound or incision in the eye until the working end tips are fully through the small incision. The forceps are then slowly opened while slowly being moved through the wound to maintain what will be called the crossover point of the intermediate sections at the incision. The moving, small-in-width crossover point allows insertion without undue or damaging stretching or friction with respect to the small incision. As the forceps tips reach the desired location in the interior of the eye, they are fully opened causing the sling to flatten out which releases (and in a controlled fashion propels or ejects) the lens into the eye cavity. The lens, by its resiliency, unfolds and can be manipulated into position for implantation.

In a reverse fashion, the forceps and sling are slowly withdrawn through the opening as they are slowly closed down so that the crossover point in the intermediate section is always at or near the opening in the eye. Finally, the working end tips are withdrawn and the sling is then removed. If the sling falls off inside the eye, it can be removed by pulling on a tail of the sling which is always maintained, at least in part, outside the eye.

The sling is made of a gentle-to-the-eye, inert, resilient material which assists in holding the folded or curled lens in as tight a configuration as possible, yet its resilient nature is such to allow a controlled release and opening of the lens as the forceps tips open within the eye. It can then be easily removed from the eye. The sling is gentle on the lens, thus reducing the risk of any scratching or damage to the lens. It also can be disposable because of its economical nature.

The sling is preferentially a tubular piece or sleeve of resilient material. It has an elongated length sufficient to encapsulate a folded or curled up intraocular lens. The tips of the crossover forceps are insertable through the tubular sling and, when spread apart to an open position, stretch the sling out to present basically a platform surface upon which the lens can be laid. The resilient nature of the sling allows the lens to be folded within the sling. The forceps tips can then be brought together to lock the folded lens within the resilient sling. Once inserted in the eye, the opening of the forceps tips coincides with the controlled unfolding of the lens. The resilient nature of the sling assists in ejecting and unfolding the lens within the eye, but does so in a controlled, gentle fashion. The lens is not thrown or exploded into the eye.

The exact configuration of the crossover forceps can vary. Generally, however, the forceps handles or arms have base ends connected to a base, and front ends connected to the forceps tips.

An intermediate portion between each tip and its respective handle provides the crossover nature of the forceps of the present invention. The intermediate portion includes at least one bent sections of which, if viewed from above or below, extends from the front end of its own handle first towards the opposite handle at its intermediate portion, and overlaps the opposite handle at the intermediate portion to connection with the outer or working end of the tip. Each of these intermediate portions therefore, instead of extending straight between the handle and the tip working end (as in conventional forceps), are basically mirror images of each other but overlap each other when the tips are brought together. The intermediate portions are slightly offset from one another, when viewed from the side, so that when the forceps are closed, and the working ends of the tips come together, the intermediate sections pass one slightly over the other; or in other words, crossover one another.

The intermediate portion of each handle "crosses over" each other in at least one place when the handles are brought together. A crossing point is located adjacent the working tips. At the point where the intermediate sections cross over one another, the cross-sectional width of that portion at that crossing point is as narrow as basically the width of one of the intermediate portions. In other words, the crossing point consists of a constricted point which is narrower than if the intermediate sections were side-by-side. This crossing point or constricted point moves as the forceps are opened and closed.

As the forceps are operated from the closed position outwardly when inserting an intraocular lens into an eye, the crossing point moves along the intermediate portions of the forceps until the intermediate portions separate and do not overlap one another. Thus, this constricted crossover point provides a narrow width which can advantageously be used when inserting the forceps through the small incision. As the working end tips pass through the small incision, the forceps can be opened slightly and the constricted crossover point can be maintained at the position of the small incision, allowing the forceps to enter further in through the incision. Thus, the forceps utilize the crossover point to allow insertion of the folded or curled up lens through the small incision, and then easily and controllably release it as the forceps are pushed further through the incision.

Likewise, when desired to remove the forceps, the constricted crossover point is maintained at the small incision, while the forceps are simultaneously closed as they are pulled out.

The dimensions of the working end tips and intermediate portions can be configured to produce various depths of insertion, and widths of operation. The general concept, however, is to overcome the obstacle of conventional forceps whereby their opening and closing while being inserted through an opening is limited by the width of the incision.

BRIEF DESCRIPTION OF THE DRAWINGS

FIG. 1 is a perspective view of one embodiment of a crossover forceps for the present invention.

FIG. 2 is a top plan view of FIG. 1.

FIG. 3 is a side elevational view of FIG. 1.

FIG. 4 is an isolated top plan view of the forceps tips of FIG. 1 in a closed position (in FIGS. 1-3 the tips are in the open position).

FIG. 5 is a sectional view taken along lines 5—5 of FIG. 2.

FIG. 6 is a perspective depiction of a soft, pliable artificial replacement lens for a human eye.

FIG. 7 is a partial perspective view of the working ends of the forceps according to the embodiment of FIG. 1, and also depicting in perspective, a tubular resilient sling into which the working end tips of the forceps can be inserted.

FIG. 8 is similar to FIG. 7 except it depicts in perspective the forceps in their normally open position with the sling stretched across the working end tips to provide a platform onto which can be placed the lens of FIG. 6. Additionally, the working end of a depressor tool is partially shown.

FIG. 9 is similar to FIGS. 7 and 8 showing how the depressor tool is utilized to fold the lens within the sleeve as the forceps tips are brought together.

FIG. 10 is a cutaway view of a human eye in association with forceps according to the embodiment of FIG. 1 holding a lens in a folded-up position within the sling ready for insertion into the eye.

FIG. 11 is a front view of the eye in association with the forceps as in FIG. 10, and showing the position of an incision or wound allowing access to the interior of the eye.

FIG. 12 is a sectional view taken along lines 12-12 of FIG. 10, depicting initial insertion of the working ends of the forceps, sling, and replacement lens through the incision.

FIG. 13 depicts the continuing insertion of the forceps into the eye and the arrival of the crossover point of the forceps at the small incision.

FIG. 14 depicts the continued insertion of the forceps into the eye and the simultaneous gradual opening of the forceps with the crossover point maintained at the incision.

FIG. 15 shows the continued insertion of the forceps within the eye and the complete opening of the forceps within the eye. At this point, the lens is released within the eye.

FIG. 16 depicts the beginning of withdrawal of the forceps from the eye through the incision.

FIG. 17 depicts the complete removal of the forceps from the eye, leaving the lens within the eye.

FIG. 18 is a perspective view of another embodiment of a crossover forceps for the present invention, similar to the view of the embodiment shown in FIG. 1.

FIG. 19 is a top plan view of FIG. 18, including a resilient sling shown in broken lines.

FIG. 20 is a side elevational view of the embodiment of FIG. 18.

FIG. 21 is an enlarged partial view the embodiment of FIG. 18 showing the working end tips in a closed position, including a resilient sling shown in broken lines.

FIG. 22 is a sectional view taken along lines 22-22 of FIG. 21 showing the sling and schematically showing a folded replacement lens held in the sling.

DETAILED DESCRIPTION OF THE PREFERRED EMBODIMENTS

Preferred embodiments of the invention will now be described in detail. This description is to aid in an understanding of the invention. The description will refer to the drawings and reference numerals will be utilized to identify parts or features in the drawings. A crossover forceps will first be described in detail followed by a description of how that forceps can be used in the implantation of an intraocular lens in ophthalmic surgery.

With particular reference to FIG. 1, there is shown a crossover forceps 10 in accordance with the present invention. Forceps 10 consists of a base 12 from which extend handles 14 and 16, each being generally parallel and spaced apart along a longitudinal axis 18 of forceps 10.

In this embodiment, base and handles 14 and 16 are made of a single piece of stainless steel which is created by cutting the basic shape with an EDM machine. Such a machine is also known as an electrical discharge machine, such as is well known in the art. A more complete explanation of EDM is set forth in the commonly owned U.S. Pat. No. 4,761,028, issued in the name of Dulebohn.

In the embodiment of FIG. 1, the rear portions of handles 14 and 16 attached to base 12 are basically uniform in thickness, rectangular in cross section, and fairly thin portions which extend to thickened gripping portions 24 and 26. Gripping portions 24 and 26 have basically semicircular outer surfaces which contain raised projections 28 to enhance gripping. The rounded outer surfaces facilitate easy rotation of forceps 10 within the user's hand.

The inner side of handle 14 contains matching outwardly projecting stops 30 and 32. These two pairs of stops are raised members which abut one another when the forceps are brought to a closed position. The stops are accurately machined so as to come into abutment when the working end tips of the forceps come into abutment. Stops 30 and 32 operate to prevent gapping of the working end tips by preventing more than minimal pressure on the tips.

The interior side of handles 14 and 16 also include an anti-splay combination to eliminate splay in the forceps and therefore allow accurate and reliable operation of the forceps. A pair of parallel flanges 36 and 38 extend from opposite sides of the interior side of handle 14 towards indents 40 and 42 on opposite sides of handle 16. When handles 14 and 16 are brought towards the closed position, flanges 36 and 38 engage indents 40 and 42 and prevent any misalignment of handles 14 and 16 from that point until complete closure when stops 30 and 32 come into abutment. This in turn allows the precise and reliable operation of the working ends of the forceps.

The working end of forceps 10 consists of two elongated distal ends 44 and 46 which comprise the working end forceps tips for forceps 10. In the preferred embodiment, distal ends 44 and 46 are basically parallel and move within generally the same plane. These working ends 44 and 46 can move from the open position in FIG. 1 to the closed position shown in FIG. 4.

FIG. 1 also shows that there are intermediate portions 48 and 50 between distal ends 44 and 46 (working ends 44 and 46), and the front ends 52 and 54 of handles 14 and 16. Intermediate portions 48 and 50 are basically bent portions having a first section 56 and 58 respectively which extend angularly towards each other, that is in FIG. 1 towards the longitudinal axis 18 as shown in that position, to midpoints 60 and 62 which are closely adjacent in FIG. 1. Second sections 64 and 66 then extend away from midpoints 60 and 62 respectively and connect into working ends 44 and 46. It is to be understood that intermediate portions 48 and 50, with this bend or angular orientation, allow the "crossover" orientation of the tips of forceps 10 as will be described in more detail below.

It is also to be understood that in the preferred embodiment of FIG. 1, the tips of forceps 10 can be separate pieces which are interchangeable onto handles 14 and 16. As can be seen in FIG. 1, intermediate portions 48 and 50 are securely fastened to handles 14 and 16 by utilizing a key member 68 and 70 which can be interference fitted into a receiving slot 72 or [74] in respective handles 14 or 16. The configuration of shoulders [74] and 76 with the key and slot arrangement allow for a secure and reliable connection.

FIG. 2 depicts a normally open position for forceps 10. It can be seen that portions 20 and 22 of handles 14 and 16 are either formed or forcibly bent to angle slightly away from each other. This presents the resilient spring action holding forceps 10 in the open position. In the open position in FIG. 2, working ends 44 and 46 are spread apart as shown.

FIG. 3 depicts in additional detail the gripping portions 24 and 26 of the handles 14 and 16 forceps 10, and the key members 68 or 70 in receiving slots 72 or 74 for forceps tips to the forceps handles. Additionally, it can be seen that in the preferred embodiment, not only are the first and second sections 56, 58 and 64, 66 of intermediate portions 40 and 50 bent in the manner described previously, they are also bent in a second direction so that a plane, taken along broken line 78 and perpendicular to the page containing FIG. 3, is oblique to the longitudinal axis 18 of forceps 10. In other words, the working end tips 44 and 46 are angularly orientated to the longitudinal axis 18 in forceps 10.

FIG. 3 shows specifically that intermediate portions 48 and 50 are offset from one another so that they can overlappingly pass over one another when forceps 10 are brought towards the closed position such as shown in FIG. 4.

In FIG. 4, it can be seen how the overlapping takes place. The tips of forceps 10 basically cross at two locations, which shall be referred to as the crossing points 80 and 82. By crossing at these two locations, the forceps tips basically form a "double-x" arrangement when viewed from the angle shown in FIG. 4. In this embodiment, intermediate portion 50 crosses over intermediate portion 48. However, working ends 44 and 46 move within generally the same plane and come into abutment along their lengths (see also FIG. 3).

It is to be understood that the unique shape of the tips of the forceps, with their crossover portions, allows the working ends 44 and 46 to function like conventional forceps tips. When handles 14 and 16 are in the normally open position in FIG. 2, working ends 44 and 46 are spaced apart and biased to that open position by the spring action of base 12 and handles 14 and 16. When it is desired to close the working ends 44 and 46, handles 14 and 16 are brought together by overcoming the biasing force. The working ends 44 and 46 are operated by the user controlling handles 14 and 16.

FIG. 4 depicts a unique feature of the forceps. Although the width laterally between the midpoints 60 and 62 of the intermediate portions 48 and 50 is actually quite a bit wider than the width across front ends 52 and 54 of handles 14 and 16 when forceps 10 are in the closed position, the front crossing point 82 can be very narrow because of the configuration and the overlapping nature of the intermediate portions 48 and 50. Furthermore, the overlapping nature and shape of the intermediate portions 48 and 50 provide that the forward. crossing point 82 moves along the second sections 64 and 66 of the intermediate portions 48 and 50 as the working ends 44 and 46 are opened or closed. (This allows the working ends 44 and 46 to be inserted through a small surgical incision or wound up onto forward crossing point 82.) The entire tips of forceps 10 can then be continued to be moved inwardly through the small incision by allowing the forceps to slowly open, and crossing point 82 to move along second sections 64 and 66. This assumes, of course, that working ends 44 and 46 can move apart in whatever cavity exists on the other side of the small opening.

FIG. 3 also depicts how this unique structure and its advantageous function can be utilized where the intermediate portions 48 and 50 are angled or bent in other directions such as described with respect to the offset of plane 78 from longitudinal axis 18. For example, this offset along plane 78 provides flexibility for the surgeon as to position of handles versus orientation of the working end tips. The working end tips can be rotated around longitudinal axis 18 by merely rotating handles 14 and 16 within the surgeon's hand. A variety of different orientations for the tips can then be accomplished with minimal movement. It is to be understood, however, that the relationship of plane 78 to longitudinal axis 18 as shown in FIG. 3 can be varied according to desire.

It is further to be understood that the precise shape of the intermediate portions, first and second sections, bend points, and working ends can be varied or modified while staying within the scope of the invention. FIGS. 1-4 show only one particular such configuration.

FIG. 5 shows in more detail how the anti-splay combination of the embodiment of FIGS. 1-4 functions. Flanges 36 and 38 are spaced apart to pass into indents 40 and 42 when handles 14 and 16 come within a certain distance of one another. Once flanges 36 and 38 are within indents 40 and 42, the handles are basically locked against any transverse movement with respect to one another. This allows very precise working end operation for very small forceps ends. It also prevents any splaying between the handles or the tips. This is particularly important in the preferred embodiment having the rounded outer gripping portions 24 and 26 which allows the forceps 10 to be easily and quickly rotated within the surgeon's hands and fingers.

The method of use of the forceps 10 according to the present invention will now be described. Reference should be taken to FIGS. 6-17. The crossover forceps 10 of FIGS. 1-5 are particularly useful in the delivery of a soft, pliable artificial intraocular lens to a human eye for lens replacement. FIG. 6 shows an example of an intraocular lens 84. In the preferred embodiment this can be an IOGEL ® intraocular lens available from Alcon Laboratories, Inc., Fort Worth, Texas 76134. Lens 84 is somewhat elongated in shape (and somewhat rectangular or elliptical). It is to be understood that the lens must be foldable and somewhat resilient, so it unfolds upon release of folding forces, which is true of the IOGEL ® lens.

According to the present method, a tubular sleeve or sling 86 having a tail 88 is positioned so that working ends 44 and 46 of forceps 10 can be inserted therethrough in the orientation shown in FIG. 7. The normal inside diameter of sling 86 is less than the width across working ends 44 and 46 of forceps 10 when they are in the normally opened position. Sling 86, in the preferred embodiment, is somewhat elastomeric and can be made out of silicone rubber so that it can be stretched, yet is resilient, inert, and is gentle to the eye.

As can be seen in FIG. 8, once working ends 44 and 46 are inserted within sling 86, and forceps 10 are allowed to return to the opened position, sling 86 is stretched across the space between working ends 44 and 46. Sling 86 therefore provides a platform or surface upon which lens 84 can be placed (anterior side down), so that the longitudinal axis of lens 84 is generally parallel to the longitudinal axes of working ends 44 and 46. It can be seen that tail 88 extends from the upper side or platform of sling 86 rearwardly above intermediate portions 48 and 50 of the forceps 10.

A tool 92, in the preferred embodiment an IOGEL ® lens depressor Serial No. 8RS015, available from Alcon Laboratories, Inc., is useful for the procedure. Tool 92 has a blunt hemispherical in-cross-section end 94, the rounded part of which can be positioned over lens 84 when it is positioned on the platform of sling 86 as shown in FIG. 8. Slight pressure is then exerted by tool 92 upon the top of lens 84 downwardly, as handles 14 and 16 are moved together to close working ends 44 and 46 slowly.

As shown in FIG. 9, this creates a folding-type action to fold lens 84 within stretched-out resilient sling 86 as working ends 44 and 46 are drawn into the closed position.

Tool 92 can then be withdrawn from the envelope formed by sling 86 around lens 84. The resilient nature of sling 86 will then draw lens 84 into a tight folded position underneath working ends 44 and 46. The envelope therefore presents a small-in-cross section and narrow-in-width package which is adapted to be inserted through a small surgical incision into the patient's eye.

It is to be understood that once tool 92 is withdrawn, the configuration of forceps 10 allows the surgeon to easily rotate the forceps within the surgeon's fingers and even allow slight opening and closing to insure that the lens 84 is satisfactorily folded inside sling 86. This also allows the surgeon to orient working ends 44 and 46 and the desired direction for insertion through the incision and to have some ability to manipulate the direction of orientation of ends 44 and 46 once inside the eye.

FIGS. 10 through 17 depict a procedure for inserting the lens, now folded within the sling 86, into the eye. In FIG. 10, the eye 96 is shown in cross section including cornea 98, iris 100, and pupil 102. The surgical incision to enable the artificial replacement lens 84 to be inserted into the eye is normally made through the cornea 98 at or near the limbus 101 which is the junction between the sclera 103 and the cornea 98.

As shown in FIG. 11, the incision 104, can be made significantly smaller than with conventional methods. FIG. 11 shows in broken lines 106 the desired final position of lens 84.

FIG. 12 shows in detail how the forward-most part of working ends 44 and 46, with lens 84 folded up in substantially cylindrical form in sling 86, are inserted through the incision 104. Working ends 44 and 46 are together in the closed position, and the folded lens 84 presents a small width and cross-sectional area to insert through the incision 104. The surgeon holds the handles 14 and 16 together to keep working ends 44 and 46 closed and the lens 84 in its folded position.

FIG. 13 shows that forceps 10, in the closed position of FIG. 12, can be inserted through the incision 104 until the position shown. Any further insertion would be detrimental because the incision is not wide enough to accept second sections 64 and 66 of intermediate portions 48 and 50 of forceps 10, when forceps 10 are in the closed position shown in FIG. 13.

However, forceps 10 does allow further insertion because of their crossover nature. By simultaneously and slowly allowing handles 14 and 16 to open while at the same time slowly continuing to insert forceps 10 into the eye, it can be seen in FIG. 14 that the forward crossing point 82 on intermediate portions 48 and 50 presents a narrow enough cross section and width to avoid detrimental damage to the eye around the incision 104. Because the intermediate portions 48 and 50 cross over at crossing point 82, by maintaining that moving crossing point 82 at the incision 104, forceps 10 can be inserted further into the eye, and allowed to open far enough to release the lens 84.

As shown in FIG. 15, the crossover nature of the forceps allows handles 14 and 16 to be opened sufficiently so that working ends 44 and 46 within the eye are spread apart to the point where sling 86 with its resilient nature return to being stretched across working ends 44 and 46. This allows the lens 84 to be released from its folded position. The unfolding of the lens 84 is assisted both by its resilient nature and by the resilient nature of sling 86, which actually assists in gently forcing or propelling lens 84 outwardly into the eye. The combination of opening of the working ends 44 and 46 slowly, with the somewhat resilient unfolding of lens 84, assisted by the resilient sling 86, controls the rate of release of lens 84 so that it does not pop or explode out of the restrained position. Rapid release could cause trauma and possible damage.

It is to be understood that during this entire process, tail 88 of sling 86 extends rearwardly from working ends 44 and 46 through incision 104 and remains at least in part outside the eye.

FIG. 16 shows that once working ends 44 and 46 are opened to the point where lens 84 becomes unfolded, they can be slowly withdrawn by simultaneously and slowly closing handles 14 and 16 and withdrawing forceps 10 slowly from the eye. Again, forward crossing point 82 must be maintained at or near the surgical incision 104 to allow this retraction to happen without detriment to the incision or wound 104. Working ends 44 and 46 therefore converge underneath lens 84 and within sling 86 and can be withdrawn from the incision 104 and the eye.

As shown in FIGS. 16 and 17, sling 86 may fall off or for other reasons not adhere to forceps 10 when they are removed from the eye. Tail 88 is thus easily utilized to gently withdraw the flexible sling 86 through incision 104.

FIGS. 18-22 depict another embodiment of forceps according to the present invention. By referring to FIG. 18, forceps 108 are shown including base 110 from which extend spaced apart handles 112 and 114. Replaceable working ends 116 and 118 comprise crossover tips which function similarly to those described with respect to forceps 10 in FIGS. 1-17.

Forceps 108 presents a slightly different single piece base 110 and handles 112 and 114. Handles 112 and 114 are rectangular in cross-section having portions 120 and 122 with raised ridges 124 and 126. This also allows working ends 116 and 118 to be in a normally open position but allows convergence of ends 116 to 118 upon convergence of handles 112 and 114. Ridges 124 and 126, on the outer sides of handles 112 and 114, allow for easy maneuverability of the forceps within the surgeon's hands. Opposite stops 128 and 130 exist on the inside of handles 112 and 114 and serve to stop closing movement between handles 112 and 114. Stops 128 and 130 are configured so as to allow the distal parts of working ends 116 and 118 to come adjacent to one another. Forceps 108 differs from forceps 10 in that stops 128 and 130 allow tips or ends 116 and 118 to move parallelly adjacent to one another in substantially the same plane, but not abut one another. Stops 128 and 130 also prevent ends 116 and 118 from gapping.

The major distinction of forceps 108 with forceps 10 is the shape of intermediate portions 132 and 134. In forceps 10 (see specifically FIG. 4), first sections 56 and 58 of intermediate portions 48 and 50 extend to midpoints 60 and 62. Second sections 64 and 66 then extend from midpoints 60 and 62 to working ends 44 and 46. Midpoints 60 and 62 comprise basically bend points between first and second sections 56, 58 and 64, 66.

In forceps 108, extended sections 136 and 138 exist in intermediate portions 132 and 134. Therefore, sections 140 and 142 extend from handles 112 and 114 to extended sections 136 and 138 The opposite ends of extended sections 136 and 138 are connected to second sections 144 and 146 which are in turn connected to working ends 116 and 118.

The extended sections 136 and 138 provide a longer distance between sections 140, 142 and working ends 116 and 118 than the counterparts in forceps 108. This increases the extent to which the working end tips 116, 118 of forceps 108 can be inserted into the eye over forceps 10. Additionally, as can be seen by referring to FIG. 21, this longer distance also provides a narrower profile along the longitudinal axis of forceps 108. Forceps 108 function essentially the same as forceps 10 in their use for inserting an intraocular lens 84 into an eye. Their different shape at their intermediate sections may be preferable over forceps 10 for different uses. Additionally, it is believed that forceps 108, by not allowing working ends 116 and 118 to come together in abutment, further protects lens 84 from possible damage. It is to be understood, however, that by extending stops 30 and 32 of forceps 10, working ends 44 and 46 in that embodiment could also be disallowed from coming into abutment with one another.

It can therefore be seen that the invention achieves at least all of its stated objectives. Forceps 10 and 108 are examples of ophthalmic microsurgical tools which can be utilized with sling 86 to fold and insert lens 84 through a small incision in the eye. The forceps and sling avoid the risks of scratching or damaging a replacement lens, and allow for minimal width incisions. The combination also gives a substantial degree of maneuverability and flexibility for the surgeon, as well as a controlled release of the lens into the eye.

It will further be appreciated that the present invention can take many forms and embodiments. The true essence and spirit of this invention are defined in the appended claims, and it is not intended that the embodiments of the invention described in detail herein should limit the scope thereof.

What is claimed is:

1. An apparatus for insertion of an intraocular lens into a patient's eye comprising:
    manipulating tool means for holding and transporting the lens through an incision into the eye and releasing the lens in the eye;
    a sling means having an elastromeric resilient surface and connection means for attachment to the manipulating tool means and being resilient to extend to substantially encapsulate the lens when folded upon itself;
    the surface of the sling means being adapted to receive and substantially encapsulate a lens folded upon itself; and
    the manipulating tool means being adjustable between a first position where the connection means allows manipulation of the sling means to encapsulate and hold the lens within the sling means, and a second position where the connection means allows manipulation of the sling means to resiliently open to receive the lens before insertion into the eye, and to release the lens from its folded state once in the eye.

2. The apparatus of claim 1 further including a lens which comprises a soft, pliable, resilient intraocular lens.

3. The apparatus of claim 1 wherein the sling means has a width which can be extended laterally at least the width of the lens.

4. The apparatus of claim 1 wherein the sling means comprises a generally rectangular piece.

5. The apparatus of claim 1 wherein the sling means comprises a generally tubular piece.

6. The means of claim 1 wherein the sling means includes a tail extending so as to at least partially remain outside of the eye upon insertion and release of the lens within the eye.

7. The apparatus of claim 1 wherein the manipulating tool means includes:
   (a) means for laterally stretching the sling means;
   (b) means for positioning the sling means to substantially encapsulate the lens when folded upon itself;
   (c) means for controlling stretching of the sling means and positioning of the sling means to encapsulate the lens; and
   (d) means for controlling conversion of encapsulation of the lens to stretching of the sling means to release the lens within the eye.

8. The apparatus of claim 7 wherein the manipulating tool means comprises crossover forceps including forceps tips, crossover intermediate sections, and handles, wherein the forceps tips grip the sling means.

9. An apparatus for insertion of an intraocular lens into an eye comprising:
   crossover forceps having;
   (a) generally parallel spaced apart handles;
   (b) spaced apart parallel tips movable between a normally biased open position and a closed adjacent position, and
   (c) intermediate crossover sections connecting each handle with a respective tip;
   a resilient sling means for receiving and holding a lens in a folded position, the sling means securable to the tips of the forceps;
   the apparatus allowing a lens in a folded position to be held within the sling means for insertion through a small incision in the eye, and for controlled release of the folded lens into its unfolded state within the eye; and
   the intermediate crossover sections of the forceps presenting a movable crossover point on the forceps comprising the point of oblique overlap of the intermediate sections of the forceps to present a narrow width and allow complete insertion of and opening of the tips inside the eye while the forceps extend through the incision into the eye.

10. The apparatus of claim 9 wherein the handles of the crossover forceps are in a plane oblique to the plane defined by the tips of the forceps.

11. The apparatus of claim 9 wherein the resilient sling means comprises a generally tubular flexible member wherein the tips of the forceps are inserted along opposite interior positions of the flexible tube.

12. The apparatus of claim 9 further comprising a lens folding tool including an elongated arm for exerting pressure against the top of the lens when in position on the sling means along an axis generally parallel to the tips of the forceps.

13. The apparatus of claim 12 wherein the lens folding tool further comprises a curved surface to assist in folding the lens and to assist in removal of the lens folding tool from the lens.

14. The apparatus of claim 13 wherein the curved surface in cross-section is semi-circular, and narrower than the width of the lens.

15. The apparatus of claim 9 wherein the sling means is removable from the crossover forceps.

16. The apparatus of claim 9 wherein the sling means includes a tail member which extends from the sling means.

17. A method for implantation of a replacement intraocular lens into an eye comprising:
   preparing a foldable platform for placement of the lens, the foldable platform being formed by a resilient tubular sleeve held in a generally taut position by first and second working ends of a crossover forceps inside the sleeve at spaced apart positions, the crossover forceps having intermediate portions extending rearwardly from the working end tips, the intermediate portions having bent sections which cross over each during closing of the forceps to provide a front crossover point at a forward position with respect to the intermediate portions;
   simultaneously applying pressure upon the lens while slowly closing the working end tips to fold the lens within the sleeve;
   bringing the working end tips into a closed position to present a small width cross-section regarding the working end tips and the lens folded within the sleeve;
   slowly inserting the working end tips and sleeve with lens folded therein, through a small incision in the eye;
   continuing the insertion of the working end tips and sleeve with folded lens until the rear of the working end tips is approached, which is the general location for the front crossover point of the intermediate sections of the forceps;
   continuing slowly insertion of the forceps tips into the eye, while simultaneously slowly opening the forceps tips, causing the crossover point to move rearwardly on the intermediate portions, so that the crossover point remains generally in the same area as the incision;
   continuing simultaneous inward movement of the forceps tips and opening of the forceps until the working ends, sleeve, and folded lens are at a desired location within the eye;
   releasing the lens within the eye by slowly opening the forceps tips while maintaining the crossover point at or near the incision;
   simultaneously slowly retracting and closing the forceps, maintaining the crossover point generally at or near the incision; and
   withdrawing the forceps, including the working ends, through the incision.

18. A method for insertion of a soft, flexible intraocular lens into a patient's eye through a small incision in the patient's eye comprising:
   making a small incision in the eye to present access to the eye's intraocular chamber;
   folding the lens within a resilient sling means so that the folded lens and sling means can pass through the incision;

holding the sling means about the folded lens to retain the lens in folded position by utilizing closed working ends of a forceps means;

inserting the sling means and folded lens through the incision with the working ends of the forceps means maintaining the lens in folded position;

releasing the lens from the folded position in the sling means when inside the eye by opening the working ends of the forceps means; and withdrawing the sling means and working ends of the forceps means from the eye through the incision.

19. The method of claim 18 wherein the stop of folding the lens comprises substantially folding the lens upon itself.

20. The method of claim 18 wherein folding the lens comprises curling the lens upon itself.

21. The method of claim 18 comprising the further step of substantially encapsulating the folded lens when held by the sling means.

22. The method of claim 18 wherein the opening of the working ends of the forceps means allows the resiliency of the sling means to assist in releasing the lens from the sling means.

23. The method of claim 18 wherein the lens has at least in part inherent resiliency which assists in unfolding the lens upon release within the eye.

24. The method of claim 18 wherein the forceps means includes an intermediate section between handles and the working ends, the intermediate section having a cross-sectional width at all times smaller than the incision.

25. The method of claim 18 wherein the sling means is made of a material which is gentle on the eye and which is substantially inert to resist irritation of either the exterior or interior of the eye.

26. The method of claim 25 wherein the sling is at least substantially made of silicon rubber.

27. The method of claim 18 wherein the incision is made at the limbus of the eye to allow access to the intraocular chamber of the eye.

28. A method of implantation of an intraocular lens into an eye comprising:

inserting a pair of forceps tips of a forceps means, the tips being movable between a spaced apart, normally biased open position and an adjacent closed position, into a generally flexible tubular resilient sling means, the open position of the forceps tips holding the sling means in a transverse extended position between the tips to present a platform for placement of the lens;

placing the lens on the platform created by the sling;

manipulating the lens within the sling to cause folding of the lens upon itself;

moving the forceps tips to the closed position to substantially encapsulate and hold the lens in a folded position;

moving the forceps means to insert the closed forceps tips and lens encapsulated within the sling through an incision in the eye; and releasing the lens within the eye by operating the forceps means outside the eye to move the forceps tips inside the eye to a substantially open position.

29. The method of claim 28 wherein the step of manipulating the lens includes:

(a) exerting pressure against the lens on the platform of the sling along an axis generally midway between and parallel to the forceps tips, stretching the sling means and causing a folding of the lens about the axis;

(b) continuing downward pressure until the lens is substantially on one side of a plane defined by the forceps tips;

(c) moving the forceps tips to the closed position to retain the folded lens and hold the folded lens within the sling; and (d) allowing the resiliency of the sling to bias the folded lens to a compact configuration.

30. The method of claim 29 wherein the pressure is accomplished by a folding tool having an elongated member to exert pressure along the axis, and which can be withdrawn without damage to the folded lens when held within the sling.

31. The method of claim 29 wherein the step of pressure against the lens is accomplished by a tool having a first elongated member for exerting pressure along the axis.

32. The method of claim 28 wherein the closed position for the forceps tips consists of the tips being substantially adjacent but not in abutment.

33. The method of claim 28 wherein the lens is resilient and pliable.

34. The method of claim 28 wherein the step of releasing the lens includes utilizing the resiliency of the sling to assist in propelling the lens from the sling.

35. The method of claim 28 comprising the further step of withdrawing the forceps means and sling through the incision from the eye after releasing the lens.

36. The method of claim 28 further comprising the step of making the incision smaller than the distance between the forceps tips in the open position.

* * * * *